(12) United States Patent
Sohn et al.

(10) Patent No.: US 8,030,506 B2
(45) Date of Patent: Oct. 4, 2011

(54) TUMOR SELECTIVE AND BIODEGRADABLE CYCLOTRIPHOSPHAZENE-PLATINUM(II) CONJUGATE ANTICANCER AGENT, AND PREPARATION METHOD THEREOF

(75) Inventors: Youn-Soo Sohn, Seoul (KR); Ji-Young Yu, Seoul (KR); Yong-Joo Jun, Seoul (KR)

(73) Assignee: Nanohybrid Co., Ltd, Seoul (KR)

( * ) Notice: Subject to any disclaimer, the term of this patent is extended or adjusted under 35 U.S.C. 154(b) by 15 days.

(21) Appl. No.: 12/595,943

(22) PCT Filed: Apr. 11, 2008

(86) PCT No.: PCT/KR2008/002068
§ 371 (c)(1),
(2), (4) Date: May 21, 2010

(87) PCT Pub. No.: WO2008/130121
PCT Pub. Date: Oct. 30, 2008

(65) Prior Publication Data
US 2010/0249226 A1    Sep. 30, 2010

(30) Foreign Application Priority Data
Apr. 18, 2007 (KR) .......................... 10-2007-0038055

(51) Int. Cl.
*C07F 15/00* (2006.01)
*A61K 31/28* (2006.01)
(52) U.S. Cl. ............. 556/17; 556/18; 556/492; 514/492
(58) Field of Classification Search .................... 556/17, 556/18, 137; 514/492
See application file for complete search history.

(56) References Cited

U.S. PATENT DOCUMENTS 6,221,906 B1 *  4/2001  Sohn et al. .................... 514/492
6,333,422 B1    12/2001  Sohn et al.

OTHER PUBLICATIONS

Lebwohl et al., "Clinical Development of Platinum Complexes in Cancer Therapy; an Historical Perspective and an Update", Eur. J. Cancer., 34, 1522 (1998).
Meada et al., CRC Crit, Rev. Ther. Drug Carrier Sys 6, 193 (1998).
Duncan, "Polymer Conjugates for Tumour Targeting and Intracytoplasmic Delivery: The EPR Effect as a Common Gateway", Pharm. Sci. Technol. Today, 2 441 (1999).
Lundberg et al., "Control of the Cell Cycle and Apoptosis", Eur. J. Cancer., 35, 531-539 (1999).
Vasey et al., "Phase I Clinical and Pharmacokinetic Study of PK1 [N-(2-Hydroxypropyl) Methacrylamide Copolymer Doxorubicin]: First Member of a New Class of Chemotherapeutic Agents Drug-Polymer Conjugates", Clin. Cancer Res., 5, 83 (1999).
Haag et al., "Polymer Therapeutics: Concepts and Applications", Angew. Chem. Int. Ed., 45, 1198-1215 (2006).
Sohn et al., "Thermosensitive Cyclotriphosphazenes", J. Am. Chem. Soc., 122, 8315 (2000).
Sohn et al., "Synthesis and Antitumor Activity of Novel Thermosensitive Platinum (II) Cyclotriphosphazene Conjugates", J. Control. Release., 90, 303 (2003).
Sohn et al., "Thermoresponsive Micelles from Oligopeptide-Grafted Cyclotriphosphazenes", Angew. Chem. Int. Edit., 45, 6173-6176 (2006).
Soyez et al., "The Crucial Role of Spacer Groups in Macromolecular Prodrug Design", Adv. Drug Deliv. Rev., 21, 81-106 (1996).
Song et al., "Synthesis, Characterization, and Tumor Selectivity of a Polyphosphazene Platinum (II) Conjugate", J. Control. Release., 105, 142-150 (2005).

* cited by examiner

*Primary Examiner* — Porfirio Nazario Gonzalez
(74) *Attorney, Agent, or Firm* — Edwards Angell Palmer & Dodge LLP; Kongsik Kim

(57) ABSTRACT

Disclosed are a novel cyclotriphosphazene-platinum(II) complex conjugate anticancer agent, showing high selectivity to tumor tissues due to the enhanced permeability and retention effect in tumor tissues and a preparation method thereof.

17 Claims, 1 Drawing Sheet

[Fig. 1]
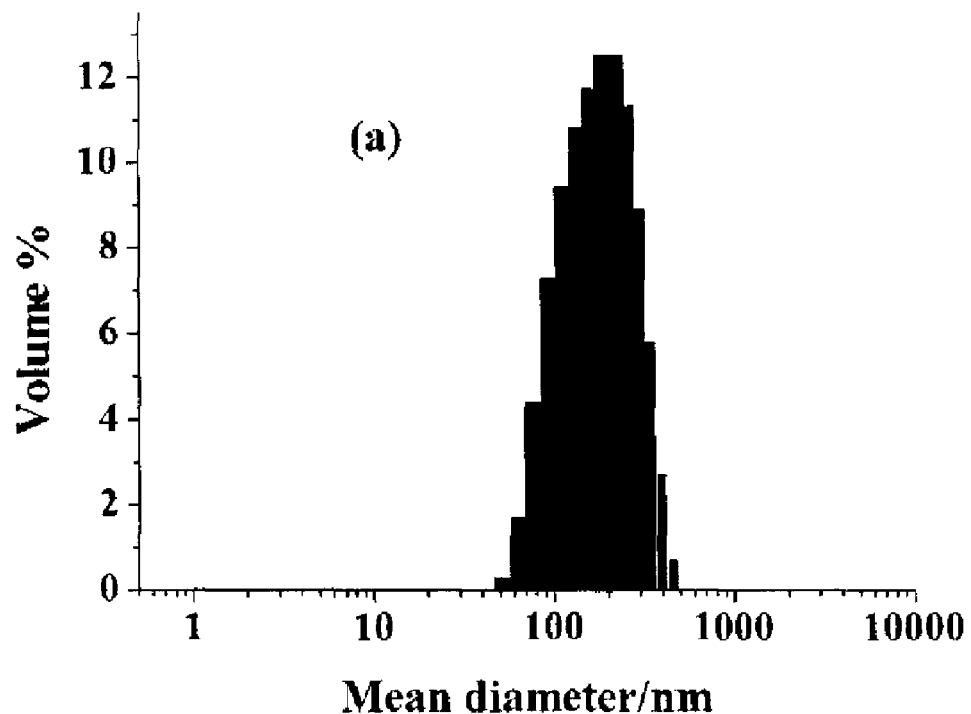
[Fig. 2]
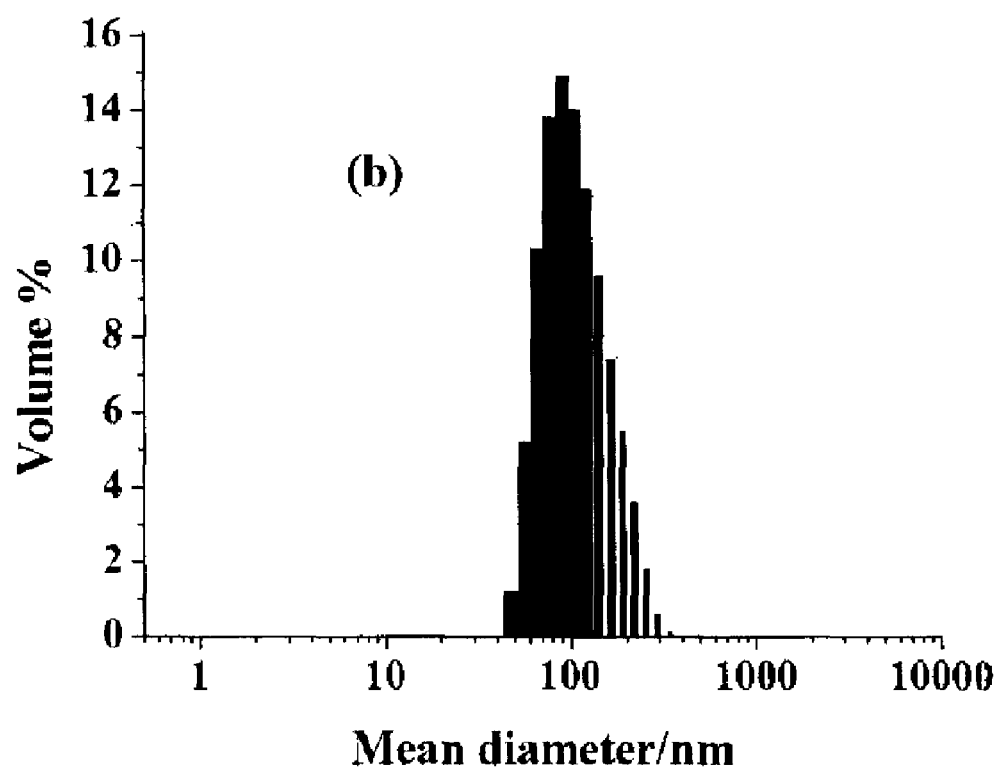

TUMOR SELECTIVE AND BIODEGRADABLE CYCLOTRIPHOSPHAZENE-PLATINUM(II) CONJUGATE ANTICANCER AGENT, AND PREPARATION METHOD THEREOF

CROSS REFERENCES TO RELATED APPLICATIONS

This application is a U.S. national phase application, pursuant to 35 U.S.C. §371, of PCT/KR2008/002068, filed Apr. 11, 2008, designating the United States, which claims priority to Korean Application No. 10-2007-0038055, filed on Apr. 18, 2007. The entire contents of the aforementioned patent applications are incorporated herein by this reference.

TECHNICAL FIELD

The present invention relates to a tumor selective and biodegradable cyclotriphosphazene-platinum(II) conjugate anticancer agent, and a preparation method thereof.

BACKGROUND ART

Platinum(II) anticancer agents such as cisplatin, carboplatin and oxaliplatin presently in clinical use are among the most widely used anticancer agents in the world. In particular, these platinum drugs have been known to exhibit superior antitumor activities against genital cancers such as testicular, ovarian, and bladder cancers as well as colorectal cancer.

However, like other low molecular weight anticancer agents such as paclitaxel, doxorubicin, etc., platinum anticancer agents administered systemically attack not only tumor cells and tissues but also normal cells and tissues equally without tumor selectivity, which cause severe toxicities such as nephrotoxicity, neurotoxicity, etc. In addition, their acquired cross-resistance and low water-solubility seriously limit their utility for cancer treatment (D. Lebwohl, R. Canetta, Eur. J. Cancer., 34, 1522 (1998)).

Accordingly, tremendous efforts have recently been made worldwide for the development of tumor targeting anticancer agents having selective cytotoxicity only on tumor cells or tissues, thereby drastically reducing adverse effects resulting from toxicity and overcoming drug-resistance. One of the most rational approaches to overcome non-selectivity and drug resistance inherently associated with the low molecular weight anticancer agents currently in clinical use is to use polymeric drug delivery systems, which have been intensively studied for the last decade. As representative examples, there are two different methods to afford the low molecular weight anticancer agents to have tumor selectivity. One is direct coupling of the conventional anticancer agents with a targeting group having a strong affinity to receptors or antigens preferentially expressed in tumor cells or tissues, or coupling both a targeting group and a conventional anticancer agent with a water-soluble polymer (Active Targeting), and the other method to confer tumor selectivity on an anticancer agent is to conjugate the small molecular anticancer agent directly to polymer particles which have not any targeting group but exhibit enhanced permeability and retention (EPR) effect in tumor tissues (Passive Targeting).

In particular, since the discovery that polymers with appropriate molecular weights show preferentially enhanced permeability and retention effect in solid tumor tissues (H. Meada, and Y. Matsumura, CRC Crit, Rev. Ther. Drug Carrier Sys 6, 193 (1989)), a great deal of researches have been performed worldwide for the development of new polymeric materials showing high tumor selectivity. Two probable reasons why polymers with appropriate molecular weights show high selectivity to tumor tissues are as follows:

The first one is that although large polymer molecules, nano-particles or the like can hardly permeate through blood vessel walls in normal tissues composed of regularly and tightly arrayed cells, they can permeate through the blood vessel pores into the tumor tissues due to the coarse vasculature of the tumor tissues, flow of a large amount of blood into the tumor tissues, and higher vascular pressure in tumor tissues.

The second one is that there is no lymphatic vessel as a discharge path for polymer particles in tumor tissues. Therefore, in tumor tissues, it is difficult for polymer particles permeated therein to be discharged unlike in normal cells (R. Duncan, Pharm. Sci. Technol. Today, 2, 441 (1999)). As a result, polymer particles permeated through the blood vessel pores are selectively accumulated in tumor tissues (H. Maeda, J. Fang, T. Inutsuka, Inter Immun., 3, 319 (2003)), yielding higher selectivity of polymers to tumor tissues.

Accordingly, a great deal of researches has been performed for the development of new drug delivery systems using specific bio-affinitive polymer materials around the world (A. S. Lundberg and R. A. Weinberg, Eur, J, Cancer, 35, 531-539 (1999)). One successful example of such attempts is neocarzinostatin bound to styrene-maleic anhydride copolymer (SMANCS), which was early developed and commercialized in Japan (K. Tsuchia, H. Maeda, Urology, 55, 495 (2000)). Furthermore, various types of polymer-drug conjugates, including a conjugate of N-(2-hydroxypropyl)methacrylamide (HPMA) and doxorubicin (P. A. Vasey, C. Twelves, Clin. Cancer Res., 5, 83 (1999)), have been developed and recently entered clinical trials (R. Haag, F. Kratz, Angew. Chem. Int. Ed., 2006, 45, 1198-1215). Therefore, it can be seen that researches in this field have been actively progressing worldwide. However, how many of such conjugate drugs can be approved finally for clinical use is questionable, because most of the conventional organic polymers used as drug carriers are not biodegradable and have not high tumor selectivity.

The present inventors discovered that cyclotriphosphazene derivatives grafted with equimolar amounts of a poly(ethylene glycol) (PEG) as a hydrophilic group and an amino acid as a hydrophobic group exhibited thermosensitive properties (Youn Soo Sohn et al. J. Am. Chem. Soc., 2000, 122, 8315), and successfully prepared a thermosensitive platinum anticancer agent therefrom for local delivery by conjugating the antitumor (diamine)platinum moiety to the amino acid of the cyclic trimer (Youn Soo Sohn et al. J. Control. Release, 90, 303 (2003); Youn Soo Sohn et al. U.S. Pat. No. 6,333,422 (2001)). However, the resultant cyclotriphosphazene-platinum conjugate drug did not exhibit tumor selectivity in the biodistribution experiment, probably because the conjugate molecules could not aggregate to form micelles or nanoparticles due to the low hydrophobicity of the amino acid employed as a hydrophobic group.

DISCLOSURE OF INVENTION

Technical Solution

Therefore, it is an object of the present invention to provide a nanoparticulate cyclotriphosphazene-platinum conjugate anticancer agent, in which a hydrophobic (diamine)platinum (II) complex is introduced into an amphiphilic cyclotriphosphazene which forms micelles in aqueous solution, capable of having higher selectivity to tumor tissues due to its enhanced permeability and retention effect in tumor tissues and having a higher antitumor activity, and a preparation method thereof.

The foregoing and other objects, features, aspects and advantages of the present invention will become more apparent from the following detailed description of the invention.

BRIEF DESCRIPTION OF THE DRAWINGS

FIGS. 1 and 2 illustrate particle size distribution of cyclotriphosphazene-platinum(II) complex conjugate anticancer agents prepared in Examples 1 and 3 respectively of the present invention in aqueous solution.

MODE FOR THE INVENTION

The present inventors have discovered that a cyclotriphosphazene derivative, in which an oligopeptide having much higher hydrophobicity compared with a simple amino acid is introduced as a hydrophobic group along with a poly(ethylene glycol) having a molecular weight of 350 or more as a hydrophilic group, forms much stronger and thermodynamically more stable micelles by self-assembly in aqueous solution, compared with conventional linear block copolymer micelles (Youn Soo Sohn et al. *Angew. Chen. Int. Edit.* 2006, 45, 6173-6176).

The present inventors achieved the objects of the present invention by discovering that a stable nanoparticulate cyclotriphophazene-platinum(II) conjugate anticancer agent having a diameter of 100-200 nm, which was prepared by hydrolyzing the aforementioned cyclotriphosphazene capable of forming strong and stable micelles in aqueous solution so as to functionalize the oligopeptide side chain, followed by chelation of a hydrophobic (diamine)platinum(II) complex to the resulting functional group of the oligopeptide side chain, exhibits higher tumor selectivity and anticancer activity. The cyclotriphosphazene-platinum(II) complex conjugate according to the present invention has biodegradability because a (diamine)platinum(II) complex is linked via an oligopeptide which is easily degraded by a peptidase present in lysosome within cells (H. Soyez et al. *Adv. Drug Deliv. Rev.* 21 (1996), 81-106).

According to the present invention, the ratio of the hydrophilicity of poly(ethylene glycol) to the hydrophobicity of oligopeptide to be introduced into cyclotriphosphazene as a drug delivery material and the degree of hydrophobicity of the (diamine)platinum(II) complex to be chelated by the oligopeptide side chain are controlled, and ethyl ester of the oligopeptide is hydrolyzed to functionalize for platination using a (diamine)platinum(II) complex anticancer agent, thereby providing a novel nano-particulate cyclotriphosphazene-platinum(II) conjugate showing an enhanced permeability and retention effect in tumor tissues as well as higher antitumor activity, and a preparation method thereof.

Therefore, the present invention relates to a cyclotriphosphazene-platinum(II) complex conjugate anticancer agent having higher selectivity to tumor tissues and higher anticancer activity, which is represented by the following Chemical Formula 1:

Chemical Formula 1:

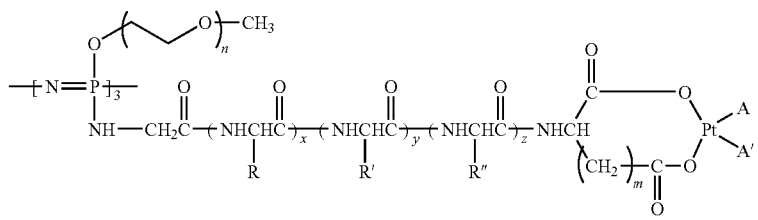

wherein n is 7, 12 or 16; m is 0, 1 or 2; x is 1; and y and z are independently 0 or 1;

R, R' and R'' are independently selected from the group consisting of $(CH_3)_2CH—$, $(CH_3)_2CHCH_2—$, $(C_2H_5)(CH_3)CH—$ and $(C_6H_5)CH_2—$; and A and A' represent two monodentate amine ligands which are identical to or different from each other, or A and A' are joined together to form a bidentate chelating diamine ligand.

If A and A' are two monodentate amine ligands, at least one of them may be a cyclohexylamine, cyclopentylamine or benzylamine, and the bidentate chelating diamine ligand may be a diamine such as trans-1,2-diaminocyclohexane (dach).

The present invention also relates to a pharmaceutical composition for treating a cancer, comprising a cyclotriphosphazene-platinum(II) complex conjugate represented by Chemical Formula 1 as an effective ingredient. The present invention also relates to a method for preparing a cyclotriphophazene-platinum(II) complex conjugate anticancer agent represented by Chemical Formula 1.

The whole reaction process for preparing the cyclotriphosphazene-platinum(II) complex conjugate of the present invention should be carried out under inert atmosphere in order to prevent moisture from the reaction system, and all solvents used for the reaction are also thoroughly dried prior to use to eliminate any trace of moisture. A coupling reaction with the platinum complex is preferably performed at any time under the state of light being blocked.

The cyclotriphosphazene-platinum(II) complex conjugate of the present invention can be prepared according to the exemplified procedures as described below.

In the first step, according to the known method (Youn Soo Sohn et al. *Angew. Chem. Int. Edit.* 2006, 45, 6173-6176), chlorine atoms of hexachlorocyclotriphosphazene $[(N=PCl_2)_3]$ having the structure shown in Chemical Formula 2 are substituted stepwise with a hydrophilic poly(ethylene glycol) having a molecular weight of 350 or more and a hydrophobic oligopeptide, for example, tri-, tetra- or pentapeptide ethyl ester, to obtain an amphiphilic cyclotriphosphazene represented by Chemical Formula 3, wherein the 3 moles of the poly(ethylene glycol) and 3 moles of the oligopeptide are used for 1 mole of hexachlorocyclotriphosphazene.

Chemical Formula 2:

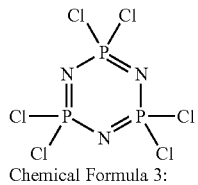

Chemical Formula 3:

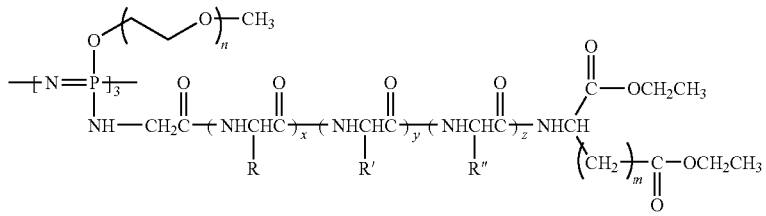

wherein n, m, x, y, z, R', R" and R are the same as defined in Chemical Formula 1.

Next, the amphiphilic trimer of Chemical Formula 3 is hydrolyzed with a base to obtain an alkaline or alkaline earth metallic salt represented by the following Chemical Formula 4.

Finally, the alkaline metallic salt or alkaline earth metallic salt of the cyclotriphosphazene represented by Chemical Formula 4 is reacted with a (diamine)platinum(II) complex represented by the following Chemical Formula 5 to obtain the cyclotriphosphazene-platinum(II) complex conjugate represented by Chemical Formula 1.

Chemical Formula 4:

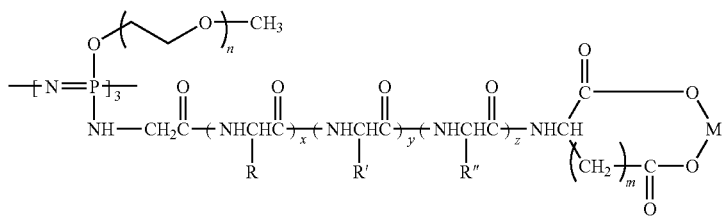

wherein n, m, x, y, z, R, R' and R" are the same as defined in Chemical Formula 1; M is two alkaline metallic ions, preferably, $2K^+$ or $2Na^+$, or an alkaline earth metallic ion, preferably, $Ba^{2+}$.

The reaction for preparing the metallic salt of Chemical Formula 4 may be carried out in a polar solvent such as water or methanol, and the base may be selected depending on the solvent for reaction with a platinum(II) complex to be performed in the next step. If the reaction between the alkaline metallic salt of Chemical Formula 4 and the platinum(II) complex is carried out in an alcoholic solvent, for example, methanol, it is preferable to use potassium hydroxide or sodium hydroxide as a base. If the reaction between the alkaline metallic salt of Chemical Formula 4 and the platinum (II) complex is carried out in aqueous solution, it is preferable to use barium hydroxide as a base. Herein, it is appropriate to use the base in an amount of 2.4 to 3.0 equiv. for one mole of oligopeptide linked to the cyclotriphosphazene represented by Chemical Formula 3.

Chemical Formula 5:

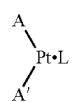

wherein A and A' are the same as defined in Chemical Formula 1; and L is one divalent anionic ligand or two monovalent anionic ligands, preferably, independently selected from sulfate ion ($SO_4^{2-}$) and nitrate ion ($NO_3^-$).

The (diamine)platinum(II) complex of Chemical Formula 5 is very important because antitumor activity as well as major physical properties such as water solubility and aggregation to nanoparticles of the compound of Chemical Formula 1 depend on the nature of (diamine)platinum(II) complex of Chemical Formula 5. In the present invention, fully considering the molecular structure of the carrier amine ligand which determines antitumor activity, hydrophobicity, solubility and the like of the platinum complex and in order to simultaneously provide superior antitumor activity and strong hydrophobicity of the conjugate, at least one of A and A' is selected from the amines having strong hydrophobicity, for example, cyclohexylamine, cyclopentylamine and benzylamine, or an amine in which A and A' are joined together to form a chelating amine, for example, trans-1,2-diaminocyclohexane (dach), is selected.

The anion L is selected from nitrate ion or sulfate ion depending on types of the salt of Chemical Formula 4 and the reaction solvent. In case of a (dicyclohexylamine)platinum (II) complex having strong hydrophobicity, its sulfate is not easily dissolved in an organic solvent but its nitrate is easily dissolved in methanol. Thus, if (dicyclohexylamine)platinum (II) nitrate is reacted with the same equivalent of an alkaline metallic salt of a cyclotriphosphazene of Chemical Formula 4 in methanol for about 6 to 12 hours, it is possible to obtain a pure compound of Chemical Formula 1. However, (amminecyclohexylamine)platinum(II) sulfate complex is not easily dissolved in an organic solvent but easily dissolved in water. Thus, if (amminecyclohexylamine)platinum(II) sulfate is reacted with the same equivalent of barium salt of Chemical Formula 4 in water, an insoluble barium sulfate is precipitated. Thus, after removing the precipitate by filtering, the pure compound of Chemical Formula 1 can be easily obtained.

The preparation method of the cyclotriphosphazene-platinum(II) complex conjugate as described above are illustrated in the following Reaction Scheme (1).

wherein n, m, x, y, z, R, R' R" A and A' are the same as defined in Chemical Formula 1; and M and L are the same as defined respectively in Chemical Formulae (4) and (5).

EXAMPLES

Hereinafter, the present invention will be described in more detail with reference to the following examples and embodiments, but it is only exemplary and not intended to limit the present invention thereto.

In the following examples, elementary analysis of carbon, hydrogen and nitrogen for the compounds of the present invention was performed using Perkin-Elmer C, H, N analyzer. Hydrogen nuclear magnetic resonance spectra were measured using Bruker DPX-250 NMR spectrometer and phosphorus nuclear magnetic resonance spectra were measured using Varian Gemini-400 NMR spectrometer. Particle size distribution of nanoparticles in aqueous solution was measured using Malvern Zetasizer (Nano-ZS).

Example 1

Preparation of tris[methoxy-poly(ethylene glycol) 550]tris[cis-dicyclohexylamineplatinum(II) glycylphenylalanylleusylaspartate]cyclo-triphosphazene, {NP(MPEG550)[GlyPheLeuAsp.Pt.cis-$(C_6H_5NH_2)_2$]}$_3$

[NP(MPEG550)(GlyPheLeuAspEt$_2$)]$_3$ (0.5 g, 0.15 mol), which was obtained according to the known method (Youn Reaction Scheme 1:

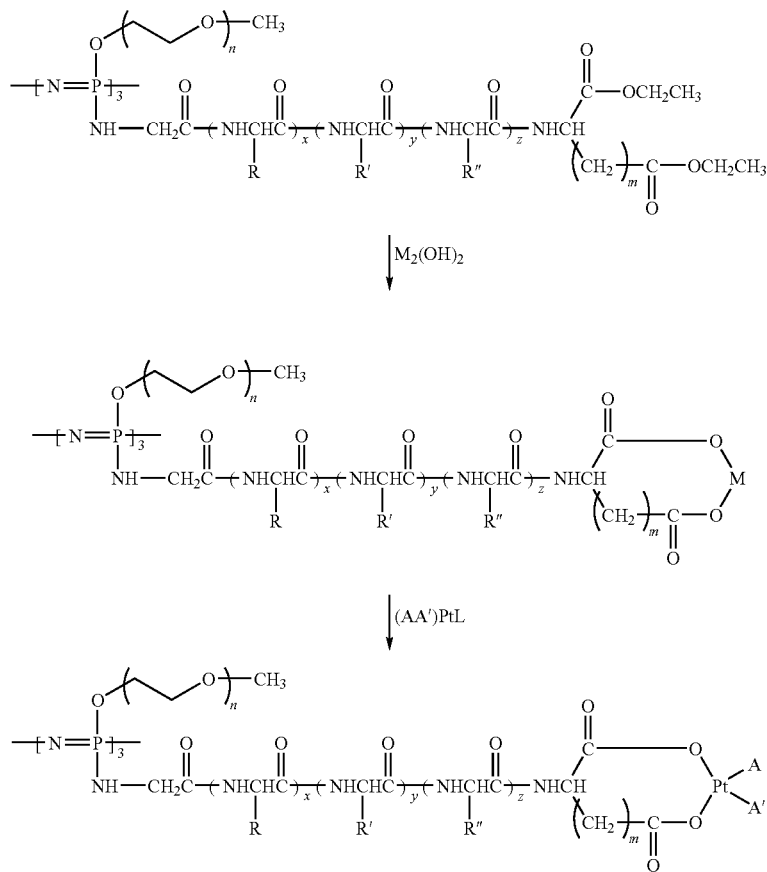

Soo Sohn et al. *Angew. Chem. Int. Edit.* 2006, 45, 6173-6176) by substituting chlorine atoms of hexachlorocyclotriphosphazene with 3 moles of methoxy-poly(ethylene glycol) having a molecular weight of 550 (MPEG550) and 3 moles of glycylphenylalanylleusylaspartic ethyl ester, was hydrolyzed with potassium hydroxide (0.11 g, 2.0 mmol) in methanol (20 ml) for 12 to 24 hours.

An excessive amount of ethyl ether or n-hexane was added to the hydrolysate so as to induce precipitation of potassium salt of [NP(MPEG550) (GlyPheLeuAspK$_2$)]$_3$. The precipitate was filtered and dried, and then reacted with (dicyclohexylamine)platinum(II) nitrate, cis-(C$_6$H$_5$NH$_2$)$_2$Pt(NO$_3$)$_2$ (0.31 g, 0.59 mmol), in methanol (20 ml) under darkness for 12 to 20 hours. The resulting reaction mixture was concentrated under vacuum to 10 ml. The concentrate was dialyzed in absolute methanol for 24 hours and in distilled water for 24 hours using a dialysis membrane (molecular weight cutoff: 500), and then freeze-dried to obtain cyclotriphosphazene-platinum(II) complex conjugate {NP(MPEG550)[GlyPheLeuAsp.Pt.cis-(C$_6$H$_5$NH$_2$)$_2$]}$_3$ in 63% yield.

Composition: C$_{174}$H$_{312}$N$_{21}$O$_{60}$P$_3$Pt$_3$
Molecular weight: 4,336.65
Elementary Analysis:
Found: C, 48.00; H, 6.85; N, 7.09. Calculated: C, 48.19; H, 7.25; N, 6.78.
$^1$NMR spectra (CD$_3$OD) (δ, ppm): 0.87 (d, 6H, Leu-(CH$_3$)$_2$), 1.12 (t, 3H, Gly-OCH$_2$CH$_3$), 1.43-1.46 (m, 2H, cyclohexylamine C-4 proton), 1.53-1.78 (m, 2H, cyclohexylamine C-6 proton), 1.39-1.49 (m, 4H, cyclohexylamine C-3, C-5 proton), 2.57 (m, 1H, cyclohexylamine, 1-C proton), 1.2-1.3 (m, 3H, Leu-CHCH$_2$), 2.95 (dd, 2H, Phe-CH$_2$), 3.2 (s, 3H, PEG350-OCH$_3$, 3.25-3.6 (b, 30H, PEG350, OCH$_2$CH$_2$), 3.65 (d, 2H, Gly-CH$_2$), 4.1 (dd, 1H, leu-CH), 4.42 (t, 1H, Phe-CH), 7.14 (m, Phe-aromatic).
$^{31}$P-NMR spectra (D$_2$O) (δ, ppm): 22.4.

Example 2

Preparation of tris[methoxy-poly(ethylene glycol) 550]tris[(cis-dicyclohexylamineplatinum(II)glycylphenylalanylleusylglutamate)]cyclo-triphosphazene, {NP(MPEG550)[GlyPheLeuGlu.Pt.cis-(C$_6$H$_5$NH$_2$)$_2$]}$_3$ The cyclotriphosphazene [NP(MPEG550)(GlyPheLeuGluEt$_2$)]$_3$ (0.5 g, 0.15 mol) and cis-(C$_6$H$_5$NH$_2$)$_2$Pt(NO$_3$)$_2$ (0.31 g, 0.59 mmol) were used in the same method as described in Example 1 to obtain {NP(MPEG550)[GlyPheLeuGlu.Pt.cis-(C$_6$H$_5$NH$_2$)$_2$]}$_3$ in 61% yield.

Composition: C$_{177}$H$_{318}$N$_{21}$O$_{60}$P$_3$Pt$_3$
Molecular weight: 4,378.73
Elementary Analysis:
Found: C, 48.12; H, 7.01; N, 7.09. Calculated: C, 48.55; H, 7.32; N, 6.92.
$^1$NMR spectra (CD$_3$OD) (δ, ppm): 0.87 (d, 6H, Leu-(CH$_3$)$_2$), 1.12 (t, 3H, Gly-OCH$_2$CH$_3$), 1.43-1.46 (m, 2H, cyclohexylamine C-4 proton), 1.53-1.78 (m, 2H, cyclohexylamine C-6 proton), 1.39-1.49 (m, 4H, cyclohexylamine C-3, C-5 proton), 2.57 (m, 1H, cyclohexylamine, 1-C proton), 1.2-1.3 (m, 3H, Leu-CHCH$_2$), 2.17 (dd, 2H, Glu-CH$_2$), 5.06 (dd, 1H, Glu-CH), 2.95 (dd, 2H, Phe-CH$_2$), 3.2 (s, 3H, PEG350-OCH$_3$), 3.25-3.6 (b, 30H, PEG350, OCH$_2$CH$_2$), 3.65 (d, 2H, Gly-CH$_2$), 4.1 (dd, 1H, Leu-CH), 4.42 (t, 1H, Phe-CH), 7.14 (m, Phe-aromatic)
$^{31}$P-NMR spectra (D$_2$O) (δ, ppm): 22.4. .

Example 3

Preparation of tris[methoxy-poly(ethylene glycol) 350]tris[(cis-amminecyclohexylamineplatinum(II) glycylphenylalanyl-leusyl-malonate)]cyclotriphosphazene, {NP(MPEG350)[GlyPheLeuMal.Pt.cis-(NH$_3$) (C$_6$H$_5$NH$_2$)$_2$]}$_3$

[NP(MPEG350)(GlyPheLeuMalEt$_2$)]$_3$ (0.5 g, 0.19 mol), which was obtained according to the known method (Youn Soo Sohn et al. *Angew. Chem. Int. Edit.* 2006, 45, 6173-6176) by substituting chlorine atoms of hexachlorocyclotriphosphazene with 3 moles of methoxy-poly(ethylene glycol) having molecular weight of 350 (MPEG350) and 3 moles of glycylphenylalanylleusylmalonic ethyl ester, was hydrolyzed with barium hydroxide (0.22 g, 0.63 mmol) in methanol (20 ml) for 12 to 24 hours.

The reaction solution was concentrated, to which an excess amount of ethyl ether was added to induce precipitation of the barium salt of cyclotriphosphazene, [NP(MPEG350)(GlyPheLeuMal.Ba)]$_3$. The barium salt was recrystallized from the same solvent system, and dissolved in distilled water (10 ml), to which cis(amminecyclohexylamine)platinum sulfate (cis-(NH$_3$)(C$_6$H$_5$NH$_2$)PtSO$_4$) (0.23 g, 0.64 mmol) in distilled water (10 ml) was slowly added. The reaction solution was further stirred at room temperature for about 12 hours, and then barium sulfate was removed by filtering. The filtrate was dialyzed in distilled water for 24 hours using a dialysis membrane (molecular weight cutoff: 500) and then freeze-dried to obtain the cyclotriphosphazene-platinum(II) complex conjugate, {NP(MPEG350) [GlyPheLeuMal.Pt.cis-(NH$_3$) (C$_6$H$_5$NH$_2$)]}$_3$ in 63% yield.

Composition: C$_{123}$H$_{216}$N$_{21}$O$_{45}$P$_3$Pt$_3$.4H$_2$O
Molecular weight: 3,387.34
Elementary Analysis (%):
Found: C, 37.72; H, 6.85; N, 8.06. Calculated (%): C, 38.68; H, 6.97; N, 7.70.
$^1$H NMR spectra (CD$_3$OD) (δ, ppm): 0.87 (d, 6H, Leu-(CH$_3$)$_2$), 1.12 (t, 3H, Gly-OCH$_2$CH$_3$), 1.43-1.46 (m, 2H, cyclohexylamine C-4 proton), 1.53-1.78 (m, 2H, cyclohexylamine C-6 proton), 1.39-1.49 (m, 4H, cyclohexylamine C-3, C-5 proton), 2.57 (m, 1H, cyclohexylamine, 1-C proton), 1.2-1.3 (m, 3H, Leu-CHCH$_2$), 2.95 (dd, 2H, Phe-CH$_2$), 3.2 (s, 3H, PEG350-OCH$_3$), 3.25-3.6 (b, 30H, PEG350, OCH$_2$CH$_2$), 3.65 (d, 2H, Gly-CH$_2$), 4.1 (dd, 1H, Leu-CH), 4.42 (t, 1H, Phe-CH), 7.14 (m, Phe-aromatic).
$^{31}$P-NMR spectra (D$_2$O) (δ, ppm): 22.3

Example 4

Preparation of tris[methoxy-poly(ethylene glycol) 350]tris[trans-1,2-diaminocyclohexaneplatinum(II) glycylphenylalanyl-leusylaspartate]cyclotriphosphazene, {NP(MPEG350)[GlyPheLeuAsp.Pt(dach)]}$_3$ The cyclotriphosphazene [NP(MPEG350)(GlyPheLeuAspEt$_2$)]$_3$ (0.5 g, 0.15 mol) and (dach)PtSO$_4$ were used in the same method as described in Example 3 to obtain {NP(MPEG350)[GlyPheLeuAsp.Pt(dach)]}$_3$ in 58% yield.

Composition: C$_{126}$H$_{210}$N$_{21}$O$_{45}$P$_3$Pt$_3$
Molecular weight: 3,423.33
Elementary Analysis (%):
Found: C, 43.75; H, 6.65; N, 8.34. Calculated (%): C, 44.21; H, 6.36; N, 8.59.

$^1$H NMR spectra (D$_2$O) (δ, ppm):0.87 (d, 6H, Leu-(CH$_3$)$_2$), 1.12 (t, 3H, Gly-OCH$_2$CH$_3$), 1.1-1.3(b, 4H, dach C-4, C-5proton), 1.5(b, 2H, dach C-3 proton), 2.1(b, 2H, dach C-6 proton), 2.3(b, 2H, dach C-1, C-2 proton), 1.2-1.3 (m, 3H, Leu-CHCH$_2$), 2.95 (dd, 2H, Phe-CH$_2$), 3.2 (s, 3H, PEG350-OCH$_3$), 3.25-3.6 (b, 30H, PEG350, OCH$_2$CH$_2$), 3.65 (d, 2H, Gly-CH$_2$), 4.1 (dd, 1H, Leu-CH), 4.42 (t, 1H, Phe-CH), 7.14 (m, Phe-aromatic)
$^{31}$P-NMR spectra (D$_2$O) (δ, ppm): 22.4

Example 5

Measurement of the Particle Size Distribution of the Compounds Obtained from Examples 1 and 3

In accordance with the procedures as described below, a dynamic light scattering (DLS) method was used to check whether the cyclotriphosphazene-platinum(II) complex conjugate of the present invention are aggregated to form stable nanoparticles in aqueous solution due to the interactions of hydrophobic groups, and to determine average particle size thereof.

The cyclotriphosphazene-platinum complex conjugates obtained from Examples 1 and 3 were dissolved in distilled water at concentrations of 0.1 to 0.5%, and the resultant solutions were subjected to DLS measurements. It was observed that nanoparticles larger and more stable than micelles were formed in aqueous solution. As shown in FIG. 1, it was discovered that the compound of Example 1 showed particles with a larger average diameter of about 200 nm probably because two cyclohexylamine ligands having strong hydrophobicity are coordinated to the platinum(II) cation. However, it was noticed that the compound of Example 3 exhibited relatively lower hydrophobicity, so as to form nanoparticles with a smaller average diameter of 105 nm, because only one cyclohexylamine ligand is coordinated to the platinum(II) cation.

Example 6

In Vivo Biodistribution Assay of Enhanced Permeability and Retention Effect of Cyclotriphosphazene-Platinum(II) Complex Conjugates Assay of tumor selectivity by the enhanced permeability and retention effect of the cyclotriphosphazene-platinum(II) complex conjugates was performed as follows:

Sprague-Dawley rats (8-9 weeks old, 250-280 g) were adopted for 4 days and then subcutaneously inoculated with 1*10$^6$ of Sarcoma-180 cells in the back region. After two weeks, when the tumor was grown up to 10 mm in diameter, the animals were classified into two groups. The cyclotriphosphazene-platinum complex conjugate prepared from Example 1 was dissolved in saline and then injected into a tail vein of the rats. The animals were sacrificed at 2 and 24 hours after the administration. Tumor tissue, normal muscle, lung, liver, kidney, and blood were collected from the animals, and their platinum concentrations were analyzed. Table 1 shows the analytical results of the platinum concentrations distributed in each of tissues and organs at 2 and 24 hours after administration of the compound of Example 1. The platinum concentration ratio of tumor tissue to normal tissue (TTR) represents the tumor selectivity due to the EPR effect. As can be seen from Table 1, the nanoparticulate cyclotriphosphazene-platinum(II) complex conjugate according to the present invention exhibit outstanding selectivity to tumor tissues.

TABLE 1

| | Platinum concentration in each of tissues and organs (mg/Kg) | | | | | | |
|---|---|---|---|---|---|---|---|
| | Normal muscle | Tumor tissue | Lung | Blood | Kidney | Liver | Ratio of tumor/normal tissues (TTR) |
| 2 hrs | 1.09 | 24.3 | 3.18 | 6.00 | 18.9 | 5.63 | 24.3/1.09 = 22.3 |
| 24 hrs | 0.23 | 19.1 | 1.56 | 1.08 | 17.3 | 6.43 | 19.1/0.23 = 83.0 |

Example 7

Assay for In Vitro Anticancer Activity Against Selected Human Cancer Cell Lines of Cyclotriphosphazene-Platinum(II) Complex Conjugates The in vitro antitumor activity of the nanoparticulate cyclotriphosphazene-platinum(II) complex conjugates prepared in Examples 1 and 3 against four main human cancer cell lines were assayed according to the known method (Rita Song et al. J. Control. Release 105 (2005) 142-150). Table 2 shows results of the in vitro antitumor activity assay of nanoparticulate platinum(II) complex conjugates prepared in Examples 1 and 3. As can be seen from Table 2, in vitro cytotoxicities of the conjugates of Examples 1 and 3 involving structurally similar aspartic acid or malonic acid, which chelated the platinum cation, were similar to those of carboplatin having a low molecular weight which was used as a standard. When considering the hydrophobicity of the prodrug according to the present invention and the enzymatic degradability of the oligopeptide, excellent in vivo antitumor activity is expected due to sustained release and excellent drug metabolism of the prodrug according to the present invention.

TABLE 2

| | In vitro cytotoxicities, IC$_{50}$ (μM) | | |
|---|---|---|---|
| Tumor cells | Carboplatin | Example 1 | Example 3 |
| MCF (breast cancer) | 48.0 | 46.7 | 26.6 |
| SK-OV3 (ovarian cancer) | 76.5 | 79.0 | 60.6 |
| A-431 (vulvar cancer) | 45.9 | 73.1 | 37.2 |
| MES-SA (uterine cancer) | 48.0 | 62.6 | 47.1 |

According to the present invention, a nanoparticulate cyclotriphosphazene-platinum(II) complex conjugate having high selectivity to tumor tissues as well as high anticancer activity has been provided. The nanoparticulate cyclotriphosphazene-platinum(II) complex conjugate according to the present invention shows a high tumor selectivity due to its enhanced permeability and retention effect, which can afford efficient treatment of cancers with minimum adverse effects, and therefore, this novel anticancer agent is expected to be widely used.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

The invention claimed is:

1. A cyclotriphosphazene-platinum(II) complex conjugate represented by the following Chemical Formula 1:

Chemical Formula 1:

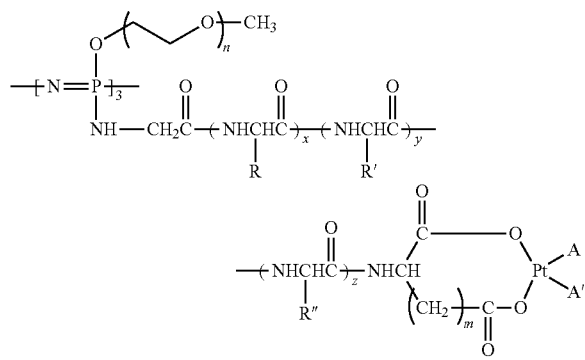

wherein n is 7, 12 or 16; m is 0, 1 or 2; x is 1, y and z are independently 0 or 1;

R, R' and R" are independently selected from the group consisting of $(CH_3)_2CH—$, $(CH_3)_2CHCH_2—$, $(C_2H_5)(CH_3)CH—$ and $(C_6H_5)CH_2—$; and A and A' represent two monodentate amine ligands which is identical to or different from each other, or A and A' may be joined together to form a bidentate chelating diamine ligand.

2. The cyclotriphosphazene-platinum(II) complex conjugate according to claim 1, wherein A and A' are two monodentate amine ligands, which is identical to or different from each other and is independently selected from the group consisting of cyclohexylamine, cyclopentylamine and benzylamine.

3. The cyclotriphosphazene-platinum(II) complex conjugate according to claim 1, wherein at least one of A and A' is cyclohexylamine.

4. The cyclotriphosphazene-platinum(II) complex conjugate according to claim 1, wherein A and A' are joined together to form trans-1,2-diaminocyclohexane.

5. The cyclotriphosphazene-platinum(II) complex conjugate according to claim 1, wherein nanoparticles with a diameter of 100 to 200 nm are formed in an aqueous solution.

6. The cyclotriphosphazene-platinum(II) complex conjugate according to claim 1, wherein molecular weight of methoxy-poly(ethylene glycol) is 350, 550 or 750.

7. A pharmaceutical composition for treating a cancer, comprising the cyclotriphosphazene-platinum(II) complex conjugate according to claim 1.

8. A preparation method of the cyclotriphosphazene-platinum(II) complex conjugate according to claim 1, comprising:
(1) hydrolyzing a cyclotriphosphazene represented by Chemical Formula 3 with a base to obtain an alkaline metallic salt or alkaline earth metallic salt represented by Chemical Formula 4; and
(2) coupling the alkaline metallic salt or alkaline earth metallic salt represented by Chemical Formula 4 with a (diamine)platinum(II) complex represented by Chemical Formula 5 to obtain the cyclotriphosphazene-platinum(II) complex conjugate of Chemical Formula 1.

Chemical Formula 1:

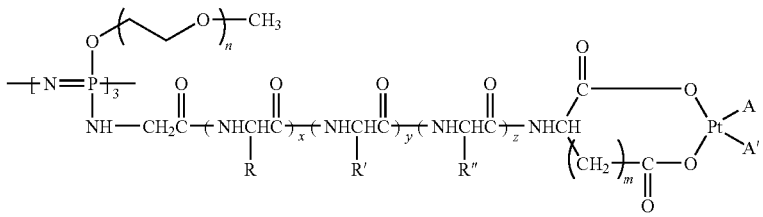

Chemical Formula 3:

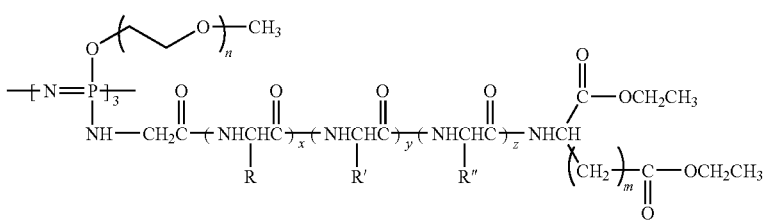

Chemical Formula 4:

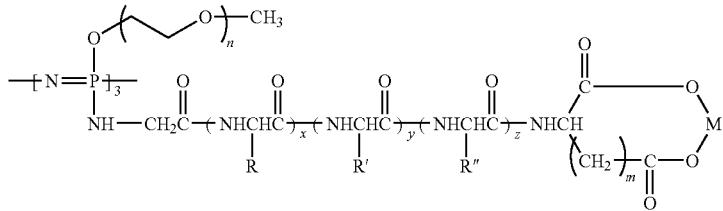

Chemical Formula 5:

wherein n is 7, 12 or 16; m is 0, 1 or 2; x is 1, y and z are independently 0 or 1;

R, R' and R'' are independently selected from the group consisting of $(CH_3)_2CH-$, $(CH_3)_2CHCH_2-$, $(C_2H_5)(CH_3)CH-$ and $(C_6H_5)CH_2-$;

A and A' represent two monodentate amine ligands which is identical to or different from each other, or A and A' may be joined together to form a bidentate chelating diamine ligand;

M represents two alkaline metallic ions selected from potassium ion and sodium ion, or $Ba^{2+}$; and L is one or two anionic ligands selected from sulfate ion and nitrate ion.

9. The preparation method according to claim 8, wherein the base is selected from the group consisting of sodium hydroxide, potassium hydroxide and barium hydroxide.

10. The preparation method according to claim 8, wherein an alcohol is used as a solvent for step (2).

11. The preparation method according to claim 8, wherein water is used as a solvent for step (2).

12. The preparation method according to claim 8, wherein the molecular weight of the methoxy-poly(ethylene glycol) is 350, 550 or 750.

13. The preparation method according to claim 8, wherein the oligopeptide is selected from the group consisting of glycylphenylalanylleusylglutamate, glycylphenylalanylleusylaspartate and glycylphenylalanylleusylmalonate.

14. The preparation method according to claim 8, wherein A and A' are two monodentate amine ligands which are identical to or different from each other and are independently selected from the group consisting of cyclohexylamine, cyclopentylamine and benzylamine.

15. The preparation method according to claim 8, wherein at least one of A and A' is cyclohexylamine.

16. The preparation method according to claim 8, wherein A and A' are joined together to form trans-1,2-diaminocyclohexane.

17. A method for treating a cancer, the method comprising using the cyclotriphosphazene-platinum(II) complex conjugate according to claim 1.

* * * * *